United States Patent [19]
Wang et al.

[11] Patent Number: 5,450,866
[45] Date of Patent: Sep. 19, 1995

[54] DENTAL FLOSS DEVICE

[75] Inventors: Gang Wang; Yi Zhang, both of Cypress, Calif.

[73] Assignee: NuPro, Inc., San Diego, Calif.

[21] Appl. No.: 229,763

[22] Filed: Apr. 19, 1994

[51] Int. Cl.⁶ .................................... A61C 15/00
[52] U.S. Cl. ............................ 132/325; 132/324
[58] Field of Search ............ 132/323, 324, 325, 326, 132/327

[56] References Cited

U.S. PATENT DOCUMENTS

| | | | |
|---|---|---|---|
| 1,512,633 | 10/1924 | Peckham | 132/326 X |
| 2,381,530 | 8/1945 | Demberski | 132/325 |
| 3,861,406 | 1/1975 | Stitt | 132/325 X |
| 3,927,687 | 12/1975 | Thierman | 132/325 |
| 4,005,722 | 2/1977 | Bragg | 132/324 |
| 4,151,851 | 5/1979 | Bragg | 132/326 |
| 4,518,000 | 5/1985 | Leverette | 132/325 |

Primary Examiner—Nicholas D. Lucchesi

[57] ABSTRACT

A dental floss device comprises an elongated handle with a U-shaped flossing head projecting from one end of the handle. A strand of dental floss originated from a supply spool containing pre-wound fresh floss passes through the flossing head and emerges back to a take-up spool for containing spent floss. Dispensing floss and providing tension on the floss are controlled by the fingers of the holding hand on both supply spool and take-up spool which are rotatably mounted on the handle. The spools are also detachably mounted on the handle so that spent floss can be discarded and the take-up spool can be cleaned at will with ease and exhausted supply spools can easily be replaced with new, pre-wound spools like cartridges thus making the device reusable.

8 Claims, 2 Drawing Sheets

DENTAL FLOSS DEVICE

BACKGROUND OF THE INVENTION

1. Field of the Invention

This invention relates in general to a dental floss device, and in particular to a reusable dental floss device that is easy to operate and inexpensive to manufacture.

2. Prior Art

Flossing teeth regularly if not daily has long been recommended by dentists and is practiced by many people around the world. The conventional way of flossing which perhaps is used by the majority of people, is simply holding or wrapping the free ends of a strand of dental floss with fingers of both hands. To floss properly, a strand of dental floss must be held taut on opposite sides of the teeth. Consequently, the user has to extend one end of the floss inside the mouth and hold the other outside while the mouth is stretched as widely open as it can to accommodate the hand holding the inside end of the floss. The floss is then passed successively between tooth pairs with the floss being kept tensioned. Anyone who has flossed knows that it is not easy to maneuver his hand inside the mouth especially for back teeth. To make flossing even more unpleasant is the mess; pulling the tensioned strand of dental floss out from between tightly fitted teeth often results in debris flying everywhere, on the face and the mirror in front since the mouth has to be wide open. Furthermore, as the floss becomes soiled or frayed, one has to replace it with a section of fresh floss. This is usually done by reeling the spent floss onto the holding fingers. As such, the hands have to hold spent or soiled floss which is wet and dirty.

Dental flossing devices/holders/applicators have been developed in attempt to make dental flossing easier and more effective. A search revealed numerous United States patents issued concerning dental flossing devices/holders/applicators. The following U.S. patents are believed to be more closely related to the current invention:

553,610,
4,460,002
5,056,540
1,306,998
4,706,694
5,060,681
1,640,607
4,790,336
5,067,503
2,187,442
4,807,651
5,069,233
3,746,017
4,051,857
5,105,840
U.S. Pat. Nos. 3,927,687, 4,094,328, 5,125,424

In considering their structure and functioning, all the dental flossing devices described in the prior art can be categorized as disposable and reusable. Despite the appearance and degree of complexity, providing tension on floss string and dispensing floss to replace frayed or soiled floss are two basic tasks every floss device has to accomplish. Devices of the disposable type are usually simple in structure and inexpensive to manufacture. Floss string is affixed to the flossing head of the device thus providing required tension and dispensing floss is accomplished by simply replacing the device with a brand new one. However, one such device can hardly last long. Once the tensioned string member becomes frayed, it can no longer be used effectively in flossing. As a result, a user usually has to use several of these disposable devices to complete full mouth flossing. As inexpensive as these devices may seem, the accumulated cost can still be substantial. And so is the impact on environment as these devices are usually made of non-degradable materials such as plastic.

On the other hand, the devices of the reusable type usually last a long time with only the floss needed to be replaced. Nevertheless, they are inherently much more complicated in structure—both tensioning and dispensing are accomplished by mechanical means involving many parts which increase the complexity of the devices as well as the cost to manufacture and to use.

Although the reusable dental flossing device disclosed in the current invention shares various features with those described by the prior art, still several features and advantages the present device possesses are patentably distinct over the prior art disclosures. Among other features and advantages, the most distinctive features are that the present device is easier and less expensive to manufacture and easier, more effective and efficient to use compared to those floss devices described by the prior art.

SUMMARY OF THE INVENTION

The primary object of the present invention is to provide a device for use in daily dental flossing which is easier and more effective to use.

It is also an object of the present invention to provide a reusable floss device which is easier and less expensive to manufacture.

The foregoing objects can be accomplished by providing a dental floss device having an elongated handle extending from a forward end to a middle section and to an after end. Projecting from the forward end is a U-shaped flossing head having a pair of narrow, elongated tines. The middle section where the thumb and forefinger rest in a natural holding position accommodates two spools; a supply spool for containing pre-wound fresh floss and a take-up spool for receiving spent floss. The spools are rotatably and detachably mounted in the middle section and protrude outwardly from the surface of the middle section so that the thumb and forefinger can touch the protruding crown of the spools and have control over the rotational movement of the spools to provide tension on the floss and to advance fresh floss from the supply spool and rewind spent floss into the take-up spool. The after end serves simply as a handle where the palm and the rest of the fingers hold in exactly the same way as one usually would a handle of a regular tooth brush.

In the arrangement described above, a strand of dental floss originated from the pre-wound supply spool extends tightly towards the tip of the forward end, spans the distance between the tips of the tines of the flossing head and emerges back to the take-up spool. Such arrangement will allow easy control on providing tension on the floss and dispensing fresh floss from supply spool and rewinding spent floss back to the take-up spool without even changing the holding position of the hand gripping the device. Tension on the floss is initially provided by rolling the supply spool and take-up spool to pull the floss until it is tight and is then preserved by pressing down the fingers on the protruding crown of both the supply and take-up spools, as one automatically does as he grips a handle firmly, to prevent the spools from rotating. When the string member at the flossing head is frayed, the user can dispense the floss by simply releasing the pressure on the spools and by rolling the take-up spool with a finger of the holding hand to pull the fresh floss out from the supply spool to the flossing head and to pull the spent floss towards and into the take-up spool simultaneously. As such, providing tension on the floss and dispensing floss require very little effort.

Detachable arrangement of the spools allows an exhausted supply spool to be replaced easily with a new, pre-manufactured and loaded supply spool thus making the device reusable. It also allows the take-up spool to be taken out and cleaned for sanitation reasons. This can be accomplished by cutting the floss near the take-up spool with a cutter which is embedded safely on the handle, then taking out the take-up spool and unwinding the spent floss from the spool. Upon completion of cleaning the take-up spool, the user engages the free end of fresh floss with the take-up spool to ensure that the floss will reel into the spool tightly and puts it back into designated position ready for use. Preferably, supply spools are identical to the take-up spools so that an empty supply spool can be used to replace a used take-up spool for, again, sanitation reasons.

BRIEF DESCRIPTION OF THE DRAWING FIGURES

DETAILED DESCRIPTION

Figure 1:
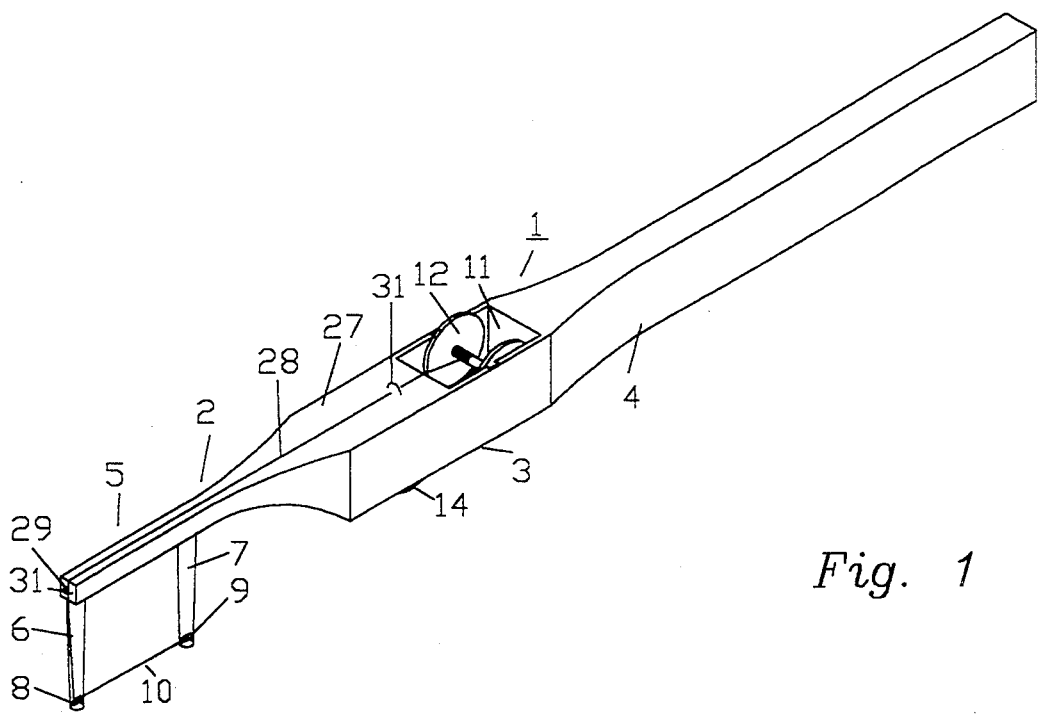
FIG. 1 is a perspective view of a dental flossing device made in accordance with the present invention.

Refer now to FIG. 1, which is an overall drawing of a preferred embodiment in accordance with the present invention. The device is made of rigid, fight weight, non-toxic and inexpensive material, and has an elongated handle 1 extending from a forward end 2, to a middle section 3 and to an after end 4. A U-shaped flossing head 5 projecting perpendicularly from the forward end 2 comprises a pair of narrow, elongated, longitudinally mounted tines; a forward tine 6 located at the tip of the forward end 2 and an after thee 7. Small holes 8 and 9 are pre-drilled at the tip of tines 6 and 7 to admit a strand of dental floss to pass through forming a working section 10 and to hold the floss in place spanning the tips of the tines 6 and 7. The tines 6 and 7 are preferably integral parts of the forward end 2 and are conical shaped to structurally reinforce stiffness of the tines towards the base to help sustain forces applied to the tines 6 and 7 from various directions during flossing.

Figure 2:
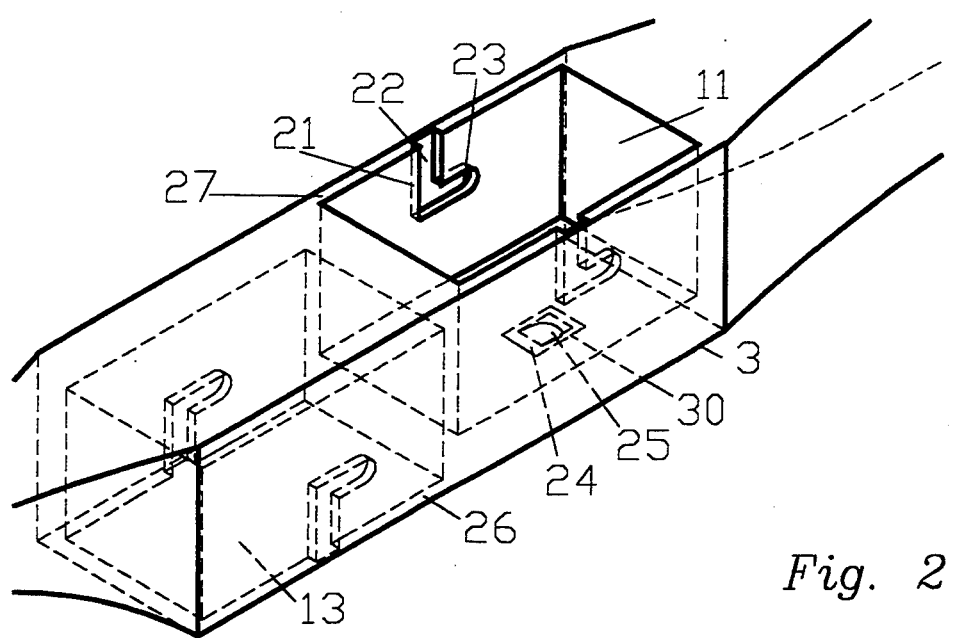
FIG. 2 is a enlarged fragmentary perspective view of the spool chambers which are identical in structure for both chambers.
Figure 3:
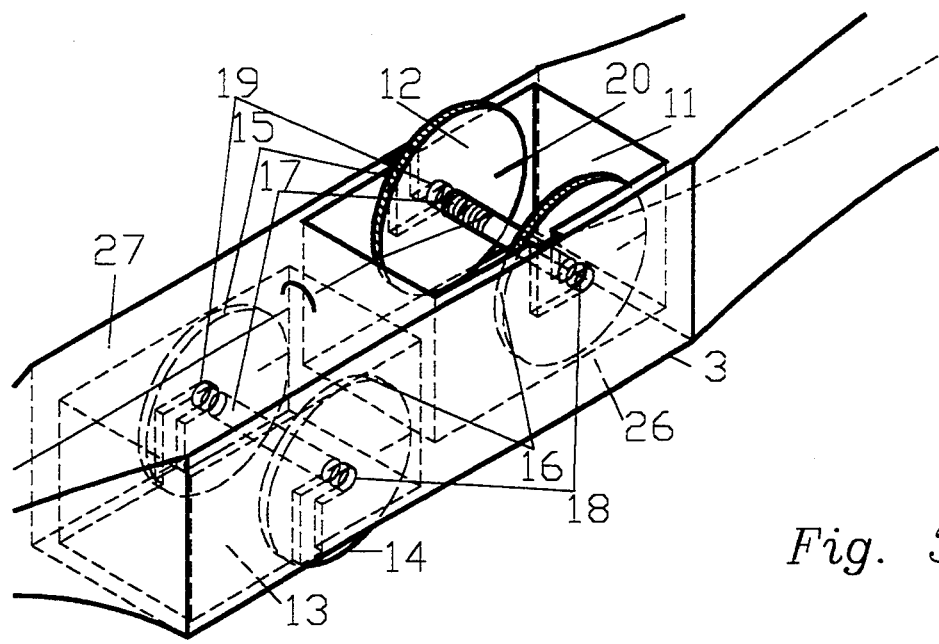
FIG. 3 is a enlarged fragmentary perspective view of the spool chambers with spools in position.

The middle section 3, shown in enlarged and fragmentary views in FIG. 2 and FIG. 3 is where the thumb and forefinger are placed in a natural way of holding a handle. It includes two identical and longitudinally positioned chambers 11 and 13 which accommodate respectively a supply spool 12 for containing pre-wound fresh floss and a take-up spool 14 for receiving spent floss. The chambers 11 and 13 are isolated from each other so as to keep the supply spool 12 from being contaminated by the take-up spool 14, and have openings cut on the upper side 27 and lower side 26 of the middle section 3 so that the thumb and forefinger of the holding hand each controls a spool.

Figure 4:
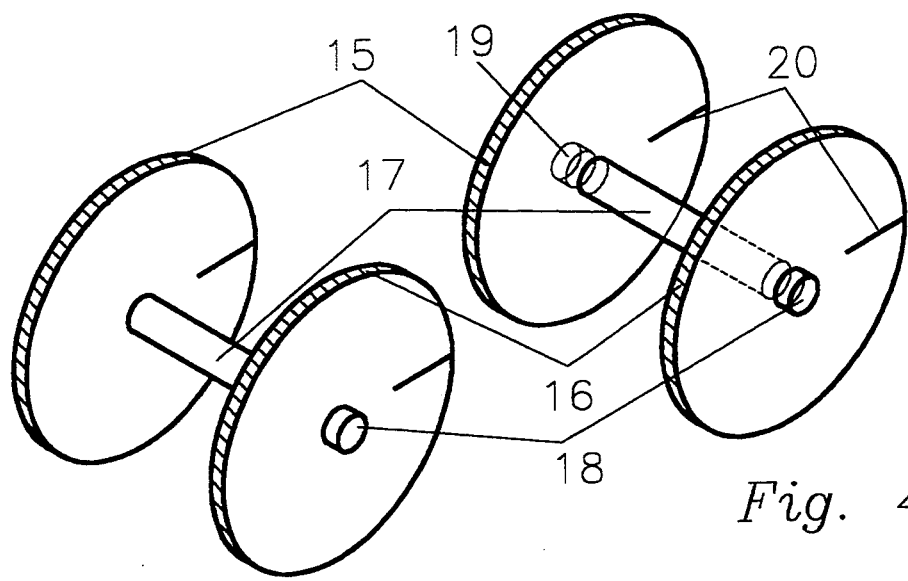
FIG. 4 is a top perspective view of the spools.

The spools 12 and 14 which can be better seen in FIG. 4 are preferably identical in structure and in shape and are made of a pair of thin round end flanges 15 and 16, an intermediate cylindrical drum 17 and two short studs 18 and 19 outwardly and coaxially mounted in the center of the end flanges 15 and 16 effectively serving as a shaft about which the spools can rotate. A short and thin slit 20 is cut partially from the out edge of flanges 15 and 16 towards the center to provide quick, easy, tight and secure engagement of a free end of a floss string with the flanges so that as the spools rotate, the floss reels onto the intermediate cylindrical drum 17 tightly and securely.

Figure 5:
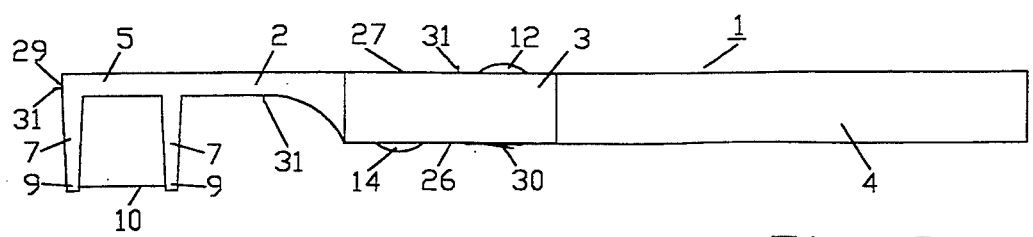
FIG. 5 is a longitudinal view of the device.

To provide easy detachment of the spools 12 and 14 into and out from the chambers 11 and 13, two L-shaped slots 21 as shown in FIG. 2 and FIG. 3 are etched onto the opposite walls of both chambers 11 and 13 so that the studs 18 and 19 on spools 12 and 14 can slide in along vertical leg 22 of the L-shaped slots 21 and sit in the end position after being pushed all the way into the end of the horizontal leg 23. As such, spools 12 and 14 can be easily installed into or removed from the chambers 11 and 13 with very little effort. Also, as the center of the spools 12 and 14 are fixed along the studs 18 and 19 in the end position of L-shaped slots 21, rotational movements of the spools 12 and 14 are allowed. Additionally, in their end position, the crown of the flanges 15 and 16 of the spools 12 and 14 protrude outwardly from the upper side 27 and lower side 26 of the middle section 3 slightly, as shown in FIG. 5, so that the fingers of the holding hand can touch the flanges 15 and 16 of the spools 12 and 14 and have control over the rotational movement of the spools 12 and 14. Furthermore, the side wall surface of the end flanges 15 and 16 of the spools 12 and 14 are preferably roughened so that the fingers have better feel on the spools 12 and 14 through friction.

A floss cutter 30, as shown in FIG. 2, made of a piece of thin metal 24 with center portion 25 preached half way open for cutting floss—an arrangement similar to the cutter used in a regular floss dispenser, is embedded on the lower side 26 on the back of chamber 11 on middle section 3. When the handle 1 is held in a hand, the cutter 30 is thus located behind and underneath the thumb and protected from the mouth.

Now, back to FIG. 1, a strand of floss 28 originated from the supply spool 12 follows a path passing along the upper side 27 of the middle section 3 towards the tip 29 of the forward end 2, spanning the distance between the tips of the tines 6 and 7 of the flossing head 5 through the holes 8 and 9 forming a working section 10, emerging therefrom along the lower side 26 of the middle section 3 and lastly back to the take-up spool 14. The spools 12 and 14 are such arranged that, when the take-up spool 14 is rolled in the direction that the floss reels on to the intermediate cylindrical drum 17 of the spool 14, fresh floss is pulled out from the supply spool 12 simultaneously to the flossing head 5 and ultimately to the take-up spool 14. To prevent the floss 28 from hanging loose and tangling, several guide eyes 31 are located along the path of the floss 28 from supply spool 12 to take-up spool 14 on the upper and lower sides of the forward end 2 and middle section 3 to keep the floss 28 attached to the surface of the forward end 2 and the middle section 3.

The after end 4 serves solely as a handle having a cross-sectional shape which is comfortable and secure to grip.

During flossing, initial tension on the floss 28 is provided by rolling the said spools 12 and 14 with the fingers of the holding hand until the floss is tight. The tension required on the floss 28 at the flossing head 5 is then preserved by pressing down the fingers on spools 12 and 14 to prevent them from rotating. When the floss at the working section 10 at the flossing head 5 is frayed or soiled, the user can dispense the floss by releasing the pressure on both the supply and take-up spools 12 and 14 and rolling the take-up spool 14 with one finger to pull fresh floss out from supply spool 12 to the flossing head 5 and, simultaneously to pull the spent floss towards and into take-up spool 14, and/or, in assisting floss dispensing, rolling the supply spool 12 with another finger. Such finger manipulation is minute and of minimum effort as only a very small section (the length between elongated tines 6 and 7 at the flossing head 5) is frayed and needs to be replaced. As the spools 12 and 14 are located in such places where the forefinger and thumb rest in a natural holding position, pressing down the fingers is a natural consequence of gripping a handle.

Finally, after finishing full mouth flossing, the user may wish to discard the spent floss and clean up the take-up spool 14 for sanitation reasons. This can be accomplished by first rewinding all spent floss into the take-up spool 14, sliding the take-up spool 14 along the L-shaped slots 21 and out of the chamber 13, then cutting the floss with the floss cutter 30, and finally unwinding the spent floss from the take-up spool 14 and throwing it away. The take-up spool 14 and chamber 13 can then be cleaned. To prepare the device for the next use, the user simply pulls the newly cut free end of the floss and engages it into the slit 20 on one of the flanges of the take-up spool 14 and slides the spool back along the L-shaped slots 21 and into the designated chamber 13. Similarly, when a supply spool is exhausted and needs to be replaced, the user simply pulls out both the empty supply spool 12 and take-up spool 14 from chambers 11 and 13, inserts a loaded supply spool 12 into chamber 11, guides the floss string along the floss path through the guide eyes 31 and small holes at the tip of the tines 6 and 7, engages the free end of the floss with the flange of take-up spool 14, and finally slides take-up spool 14 back into chamber 13.

A dental floss device described above is reusable as an exhausted supply spool can easily be replaced with a new and loaded one. It is also simple in structure; the elongated handle 1 and two spools 12 and 14 are relatively simple in shape and can easily be manufactured by manufacturing processes such as plastic injection molding. The supply spool 12 is preferably preloaded and can be supplied separately. As installing the spools 12 and 14 requires very little effort, there is no need for assembling during manufacturing process. Consequently, the device in accordance with the present invention is easy and inexpensive to manufacture. It is also simple to operate the device as described above. Providing tension on the floss and dispensing floss are at the control of finger tips and require little more effort than holding a tooth brush.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A dental floss device arranged to provide tension on floss and to simultaneously supply fresh floss and to rewind spent floss by finger manipulation, the device comprising:
    a. an elongated handle extending from a forward end to a middle section to an after end, said middle section further comprising two longitudinally extending chambers, said chambers opening and facing in opposite directions and having a closed bottom wall located within said middle section;
    b. a flossing head having a pair of elongated tines projecting from said forward end;
    c. a supply spool rotatably mounted within one of said chambers and containing pre-wound fresh floss, said supply spool being replaceable when exhausted;
    d. a take-up spool rotatably mounted within the other of said chambers for receiving spent floss;
    e. a strand of dental floss extending from said supply spool to said flossing head spanning the tips of said elongated tines and back to said take-up spool, said floss being tight to provide initial tension.

2. The dental floss device of claim 1 wherein said supply spool and said take-up spool are generally identical and include a pair of thin, round end flanges, an intermediate cylindrical drum and two short studs coaxially and outwardly mounted in the center of said flanges effectively serving as a shaft of said spools about which the spools can rotate, said spools being such arranged that rolling of said take-up spool to pull said floss into said take-up spool results in pulling of said floss out from said supply spool towards said flossing head and ultimately to said take-up spool simultaneously.

3. The dental floss device of claim 1 wherein said tines include means to allow said floss to span the tips of said tines and stay in position during flossing.

4. The dental floss device of claim 1 wherein said spools are detachably mounted in said chambers in said middle section so as to allow said supply spool to be replaced when exhausted thus making said device reusable and to allow said take-up spool to be cleaned for sanitation reasons.

5. The dental floss device of claim 1 wherein said spools are rotatably mounted in and protruding outwardly from said chambers in said middle section so that fingers of the holding hand of a user can touch said spools and have control over the rotational movement of said spools so as to preserve initial tension on said floss by pressing down on said spools thus keeping them from rotating and to dispense fresh floss by rolling said tie-up spool to pull fresh floss out from said supply spool to replace spent floss at said flossing head and to pull said spent floss towards and into said take-up spool simultaneously.

6. The dental floss device of claim 1 including means for cutting floss easily and safely when discarding said spent floss and cleaning said take-up spool is desired.

7. A dental floss device comprising an elongated handle extending from a forward end to a middle section to an after end, a flossing head having a pair of elongated tines projecting from said forward end, a supply spool for containing pre-wound fresh floss, a take-up spool for receiving spent floss, said supply spool and said take-up spool being generally identical and including a pair of thin, round end flanges, an intermediate cylindrical drum and two short studs coaxially and outwardly mounted in the center of said flanges effectively serving as a shaft of said spools about which the spools can rotate, a strand of floss following a path from said supply spool to said flossing head, across the tips of said tines and back to said take-up spool, said spools being such arranged that rolling of said take-up spool to pull said floss into said take-up spool results in pulling of said floss out from said supply spool towards said flossing head and ultimately to said take-up spool simultaneously, said floss being tight thus rendering initial tension, said middle section further comprising two longitudinally extending chambers, said chambers opening and facing in opposite directions and each having a closed bottom wall within said middle section allowing said spools to be detachably mounted so that said supply spool can be replaced when exhausted thus making said device resuable and said take-up spool can be cleaned for sanitation reasons, means carried by said middle section for said spools to be rotatably mounted and protrude outwardly for allowing the fingers of the holding hand of a user to touch said spools and to have control on the rotational movement of said spools so as to preserve the initial tension on said floss by pressing down on said spools preventing said spools from rotating and to dispense floss by rolling said take-up spool to pull fresh floss out from said supply spool to replace spent floss at said flossing head and to pull said spent floss towards and into said take-up spool simultaneously, means carried by said device for cutting said floss easily and safely when discarding said spent floss and cleaning said take-up spool is desired, and said after end having a cross sectional shape for allowing comfort and secure grip by a user's hand.

8. A dental floss device comprising an elongated handle extending from a forward end to a middle section to an after end, a flossing head having a pair of elongated tines generally projecting perpendicularly from said forward end and generally longitudinally mounted on said forward end with a forward tine generally at the tip of said forward end and an after tine, a small hole drilled generally at the tip of each of said tines, a supply spool for containing pre-wound fresh floss, a take-up spool for receiving spent floss, said spools being generally identical and including a pair of thin, round end flanges, an intermediate cylindrical dram and two short studs coaxially and outwardly mounted in the center of said flanges effectively serving as a shaft of said spools about which the spools can rotate, a thin and short slit generally cut on said flanges of said spools for quick and easy engagement of a free end of floss with said flanges so that said floss reels onto said cylindrical dram of said spools tightly and securely as said spools rotate, a strand of floss following a path from said supply spool extending towards the tip of said forward end, spanning through said holes at the tips of said tines and emerging back to said take-up spool, said spools being such arranged that rolling of said take-up spool to pull said floss into said take-up spool results in pulling of said floss out from said supply spool towards said flossing head and ultimately to said take-up spool simultaneously, said floss being tight to provide initial tension, a plurality of guide eyes being aligned along said path of said floss to prevent said floss from hanging loose and tangling, said middle section having two generally longitudinally positioned chambers to accommodate said spools, said chambers including means for said spools to be detachably mounted in said middle section so that said supply spool can be replaced when exhausted thus making said device reusable and said take-up spool can be cleaned for sanitation reasons, said chambers including means for said spools to be rotatably mounted in said middle section and for said flanges of said spools to protrude outwardly from said chambers slightly for the fingers of the holding hand of a user to touch said spools and to have control over the rotational movement of said spools through friction so as to preserve initial tension on said floss by pressing down on said spools to prevent said spools from rotating and to dispense fresh floss by rolling said take-up spool to pull fresh floss out from said supply spool to replace spent floss at said flossing head and said spent floss towards and into said take-up spool simultaneously, a sharp edged metal piece being embedded on said middle section for cutting said floss easily and safely when discarding said spent floss and cleaning of said take-up spool is desired, and said after end having such a cross-sectional shape that gripping of said after end by user's hand is comfortable and secure.

* * * * *